United States Patent
Ichihara et al.

(10) Patent No.: US 9,066,721 B2
(45) Date of Patent: Jun. 30, 2015

(54) GUT CLAMP

(75) Inventors: Takao Ichihara, Hyogo (JP); Moriatsu Takada, Hyogo (JP); Yoshikazu Kuroda, Hyogo (JP)

(73) Assignee: National University Corporation Kobe University, Hyogo (JP)

(*) Notice: Subject to any disclaimer, the term of this patent is extended or adjusted under 35 U.S.C. 154(b) by 1694 days.

(21) Appl. No.: 11/663,597

(22) PCT Filed: Sep. 22, 2005

(86) PCT No.: PCT/JP2005/017462
§ 371 (c)(1),
(2), (4) Date: Mar. 23, 2007

(87) PCT Pub. No.: WO2006/033385
PCT Pub. Date: Mar. 30, 2006

(65) Prior Publication Data
US 2007/0265644 A1    Nov. 15, 2007

(30) Foreign Application Priority Data

Sep. 24, 2004  (JP) ................................. 2004-276827

(51) Int. Cl.
*A61B 17/122* (2006.01)
*A61B 17/12* (2006.01)
*A61B 17/132* (2006.01)

(52) U.S. Cl.
CPC ........... *A61B 17/12* (2013.01); *A61B 17/12009* (2013.01); *A61B 17/132* (2013.01); *A61B 17/122* (2013.01)

(58) Field of Classification Search
CPC ...................... A61B 17/1327; A61B 2017/086; A61B 17/12; A61B 17/12009; A61B 17/122; A61B 17/132; A61B 17/1322; A61B 17/1325

USPC .......... 606/151, 157; 251/4, 9, 10; 24/17 AP, 24/30.5 P, 30.5 R, 30.5 S
See application file for complete search history.

(56) References Cited

U.S. PATENT DOCUMENTS 2,947,055 A    8/1960   McHenry
3,705,586 A   12/1972   Sarracino
(Continued)

FOREIGN PATENT DOCUMENTS

WO    WO 80/01752    9/1980
WO    WO 97/40755   11/1997

OTHER PUBLICATIONS

International Search Report for corresponding International application No. PCT/JP2005/017462 mailed on Nov. 15, 2005.

*Primary Examiner* — Jonathan W Miles
*Assistant Examiner* — Todd J Scherbel
(74) *Attorney, Agent, or Firm* — Posz Law Group, PLC (57) ABSTRACT

A gutclamper includes two hard rod-like bodies having flexible belts on one ends, a joint at which the rod-like bodies are joined, and at least one through hole made in one of the belts. The gut tract is clipped by using the two hard rod-like bodies and the joint as a pivot. By clipping the gut tract by side surfaces of the rod-like bodies, it can be clipped while the width of the gut is pressed and widened, so that the gut is prevented from being excessively clamped and torn. In addition, the two rod-like bodies are made different in length from each other, a through hole is made in the belt connected to the shorter rod-like body, and the tip end of the longer rod-like body is fit into the through hole and locked, so that reliable clipping is realized without an excessive burden being placed on an operator.

13 Claims, 5 Drawing Sheets

(56) References Cited

U.S. PATENT DOCUMENTS

| | | |
|---|---|---|
| 4,976,721 A | 12/1990 | Blasnik et al. |
| 4,988,355 A * | 1/1991 | Leveen et al. .................. 606/158 |
| 5,428,871 A * | 7/1995 | Iosif ........................... 24/30.5 R |
| 5,487,746 A * | 1/1996 | Yu et al. ......................... 606/151 |
| 5,620,452 A * | 4/1997 | Yoon ............................... 606/151 |
| 5,662,679 A * | 9/1997 | Voss et al. ..................... 606/204 |
| 5,843,101 A | 12/1998 | Fry |
| 5,921,997 A * | 7/1999 | Fogelberg et al. ............ 606/158 |
| 6,206,897 B1 | 3/2001 | Jamiolkowski et al. |
| 6,406,485 B1 * | 6/2002 | Hossain et al. ................ 606/207 |
| 6,463,932 B1 | 10/2002 | Single et al. |
| 6,596,004 B1 * | 7/2003 | Regnault ....................... 606/157 |
| 6,746,461 B2 | 6/2004 | Fry |
| 7,062,822 B2 * | 6/2006 | Folkmar ..................... 24/30.5 R |
| 7,112,221 B2 * | 9/2006 | Harris .......................... 623/13.11 |

* cited by examiner

GUT CLAMP

TECHNICAL FIELD

The present invention relates to a surgical aid instrument to be used for a surgical operation on digestive organs in principal, more specifically, a clamper which is used for gut tract resection and used for completely pressure-closing the gut tract lumen.

BACKGROUND

In laparoscopic operations, according to improvement in the techniques and improvement of instruments, it has become possible to laparoscopically perform surgical operations such as partial resection of the stomach and the large intestine and removal of bile duct calculus and cancerous tissues which could be conventionally performed only by abdominal operations. In abdominal operations, a method is used in which the gut tract is clipped with intestinal forceps during an operation for intraoperative enema cleaning or an operation for resecting the stomach or the large intestine or removing bile duct calculus or cancerous tissues.

In a laparoscopic operation, a gas for pneumoperitoneum such as carbon dioxide is supplied into the abdominal cavity via a pneumoperitoneum needle puncturing the abdominal cavity to distend the abdominal cavity, whereby a space is secured in the abdominal cavity to secure the operative field. In the method of clipping with intestinal forceps or the like as described above, for using the instrument, it is necessary to secure a sufficient space around, and it was impossible to use this method in laparoscopic operations.

On the other hand, instead of clipping the gut tract with intestinal forceps during an operation, also available is a method in which the gut tract is tied with a silk thread or tightened with a string in a ringed manner. However, this damages the gut tract frequently, and is not appropriate.

A method is considered in which the gut tract is clipped with an instrument like a clothespin. However, to effectively clamp the gut tract, a clothespin with a high spring effect must be used, and a force is needed to open the clothespin to the clipping points, and this places an excessive burden on an operator. Furthermore, around the gut, there is fat, so that in many cases using the method for clipping with a clothespin, only a half of the gut is seized, and it is impossible to confirm whether the seizing is sufficient.

Generally, as an instrument for clamping or clipping, a bundling band like an instrument to be used for bundling cable wires together is available. This bundling band tightens the gut tract in a ringed manner, and this is not appropriate. There is also available a bundling band for assisting joining of bone fragments.

Additionally, there are clip forceps for clipping a blood vessel in a human body which can be inserted in a neuroendoscope and remotely operated.

However, no matter which instrument is used, the gut tract is tightened in a ringed manner or the surrounding of the gut tract is partially clipped, and this is not appropriate.

Intraoperative dissemination due to operative maneuvers has come into question, and it is demanded that surgical operations are performed without contacting tumors.

From a medical perspective of prevention of intraluminal metastases, it is recognized as desirable that the gut tract is clamped around a tumor early in operative maneuvers.

Furthermore, as relates to intraoperative rectal lavage, in particular, in abdomino-perineal resection of the rectum, rectal lavage immediately before resection is necessary from the perspective of prevention of postoperative infection, and by clamping the rectum, it becomes possible to sufficiently clean the rectum from the anus, and as a result, the rectum can be resected at the sufficiently cleaned anus side.

From these circumstances, currently, a medical clamper which can easily, safely, and reliably clamp the gut tract during an operation for intraoperative enema cleaning or the like in the field of digestive surgery is demanded.

SUMMARY

A gutclamper of the present invention was made in view of the above-described circumstances, and an object of the invention is to provide a convenient medical clamper which can easily clamp the gut tract during an operation even in a situation where a sufficient space necessary for using instruments cannot be secured around as in the case of a laparoscopic operation, has less limitation in a movable range, and is preferable for safely performing an operation in a narrow abdominal cavity.

Another object of the invention is to provide a medical clamper which, during clamping of the gut tract, enables an operator to maneuver the clamper without an excessive burden on the operator shown in the aforementioned example using a clothespin, can clip the whole circumference instead of clipping a part of the circumference of the gut tract, and enables confirmation as to whether the clipping is sufficient.

Furthermore, in view of the problem in the method in which the gut tract is tightened by a bundling band in a ringed manner, and the gut tract is constricted and makes it difficult to identify a resection range in, for example, intestinal resection, still another object of the invention is to provide a medical clamper which can clip the gut tract by surfaces instead of tightening in a ringed manner, and can clamp the gut while widening the width of the gut.

DETAILED DESCRIPTION

The present inventors accumulated knowledge through experience of clipping the gut tract during actual operations at medical sites and repeated trial and error, and as a result, they completed the present invention. Hereinafter, means for achieving the objects will be described.

According to a first aspect of the present invention, "a gutclamper including: two hard rod-like bodies having belts with flexibility on their one ends; a joint at which the rod-like bodies are joined, and one through hole made in one of the belts" is provided.

Herein, the belts with flexibility are made of, for example, a soft resin and can be wound around the gut tract like a band, and mean string-like members as well as belt-like members.

The hard rod-like bodies are made of, for example, a hard resin, wood, or metal, and can clip the gut tract, and mean rod-like bodies with circular, oval, or polygonal sectional shapes.

The gutclamper according to the first aspect of the present invention clips the gut tract by using the two hard rod-like bodies by using the joint as a pivot. Different from the case where the gut tract is tightened in a ringed manner with a string or silk thread, this clipping method has the following advantages.

When clipping the gut tract by the rod-like bodies, the side surfaces of the rod-like bodies clip the gut tract, and as a result, the gut tract can be clipped while the width of the gut tract is pressed and widened, so that tearing of the gut due to excessive tightening as in the case of tightening in a ringed manner does not occur.

When tightening the gut tract in a ringed manner, the tightened portion is constricted like a banded bundle, so that due to the constricted portion, when observing the gut tract from the interior of the gut tract through a scope, it becomes difficult to accurately identify the resecting position, and as a result, extra portions may be resected in the gut tract resection. However, in the case of the gutclamper of the present invention, the gut tract is clipped by the rod-like bodies and the width of the gut tract is pressed and widened, and the constricted portion is reduced, so that extra portions are not resected.

Furthermore, by inserting one of the belts into the through hole of the other belt from tip end side, the two rod-like bodies can clip the gut tract by using the joint as a pivot, so that different from clipping with a clothespin, an excessive operating burden is not placed on the operator, and the whole circumference of the gut tract can be clamped while adjusting and confirming the degree of clamping.

Next, according to a second aspect of the present invention, in the first aspect of the invention, "a gutclamper wherein lengths of the two rod-like bodies are made different from each other, and the position of a through hole made in a belt connected to the shorter rod-like body is set so as to match with the tip end of the longer rod-like body when the two rod-like bodies are put together by using the joint as a pivot" is provided.

By making the lengths of the two rod-like bodies different from each other, making a through hole in a belt connected to the shorter rod-like body, and positioning the through hole at the tip end of the longer rod-like body when the two rod-like bodies are put together by using the joint as a pivot, it becomes possible to fit and lock the tip end of the longer rod-like body into the through hole by inserting the whole of a belt connected to the other longer rod-like body into the through hole from the tip end side.

According to a third aspect of the present invention, "a gutclamper which is formed of one hard rod-like body having belts on both ends, and has a through hole made in one belt" is provided.

In the gutclamper according to the first aspect described above, the gut tract is clipped by using two hard rod-like bodies, however, the gutclamper according to the third aspect uses one hard rod-like body and can clip the gut tract by the rod-like body and belts. Into the through hole made in one belt, the other belt is inserted from the tip end side, whereby the rod-like bodies and the belts clip the gut tract.

It is also allowed that one end of the hard rod-like body is formed into a belt and the other end is formed into a string.

In the first through third aspects of the present invention, the surfaces of the rod-like bodies are covered by covers made of a resin with flexibility. The surfaces of the rod-like bodies are covered by covers made of a resin with flexibility at the positions where the side surfaces of the rod-like bodies come into direct contact with the gut tract and clip it, and the covers are for protecting the surfaces of the gut tract from damage. By integrally molding belts, covers, and joint by using a soft and bendable resin, connection of the belts to the hard rod-like bodies, covering on the surfaces of the hard rod-like bodies by a flexible resin, and joining of the rod-like bodies can be concurrently and conveniently performed.

Herein, as the soft, bendable, and elastic resin, a soft resin such as a urethane resin, low-density polyethylene, etc., can be used. Instead of the resin, natural rubber or synthetic rubber may also be used.

As the integral molding, heat fusion, injection molding, thermal compression molding or bonding can be used.

As the material of the rod-like bodies, a metal such as stainless steel or a hard resin such as plastic is used. To clip the gut tract by the rod-like bodies, the rod-like bodies need to have a certain degree of hardness and strength.

The sectional shape of the rod-like bodies is circular, oval, or polygonal. To avoid a sharp contact surface so as not to damage the surface of the gut tract, the sectional shape is desirably circular or oval, however, to improve engagement for clipping by the two rod-like bodies, the sectional shape may be a polygon with unevenness or without unevenness.

The lengths of the rod-like bodies are 30 to 70 millimeters in view of the whole circumferential length of the gut tract. When the length is more than 70 millimeters, a sufficient space cannot be secured around it in a laparoscopic operation, so that it becomes difficult to use the clamper. To completely clip the whole circumference of the gut tract, it is considered that at least 30 millimeters is necessary as the length of the rod-like bodies.

In the second aspect of the present invention, the length difference between the two rod-like bodies is predetermined by considering the widths of the belts, diameters of the rod-like bodies, the diameter and arrangement of the through hole. In the case of an aid instrument for clipping the gut tract in a laparoscopic operation or the like, the widths of the belts, the diameters of the rod-like bodies, and the diameter of the through hole are several millimeters, respectively, so that the length difference between the two rod-like bodies is appropriately 3 to 7 millimeters. It is preferably 5 millimeters. By arranging the through hole so as to be positioned at the tip end of the longer rod-like body when the two rod-like bodies are put together by using the joint as a pivot, the tip end of the longer rod-like body can be fit into the through hole and locked. The size of the through hole is set so that the belt can be inserted therein. In the embodiment described later, the through hole is arranged at the portion of the length difference between the two rod-like bodies.

When using the gutclamper of the present invention, in a laparoscopic operation, the belts of the gutclamper are handled via an instrument, so that in particular, the tip end of the belt to be inserted through the through hole is tapered so as to be easily inserted through the through hole.

In the gutclamper of the present invention, by providing the belts themselves with elasticity, the belt inserted through the through hole is made more difficult to come out from the through hole, however, by further providing at least one locking portion in a projecting shape on a part of the belt to be inserted through the through hole, the belt is made more difficult to come out from the through hole after it is inserted through the through hole.

Similarly, a serrated uneven portion is provided on a part of the belt to be inserted through the through hole so as to lock the belt, whereby the belt is made more difficult to come out from the through hole after it is inserted therein.

In the gutclamper of the present invention, the color of the belts is transparent or a complementary color of red, that is, for example, blue or green, etc. This makes it possible to clearly recognize the belt seven under an environment in red of the interior of the aperture such as the gut tract and easily laparoscopically handle them.

Furthermore, in the gutclamper of the present invention, when clipping is released, the joint is seized and the one belt having the through hole is pulled, whereby the clipping can be released, and in this case, the two belts are colored differently from each other to prevent mistakes.

By using the gutclamper of the present invention, the procedure for completely pressure-closing the lumen of the gut tract by clipping the gut tract for gut tract resection under a situation where a sufficient space cannot be secured as in the case of a laparoscopic operation in digestive surgery can be conveniently, reliably, and safely performed. Of course, the gutclamper can also be used for clamping the duodenum in the case of gastric resection in a conventional general digestive surgical operation.

In addition, in the procedure for clipping the gut tract, there is no need for a force to open the clamper of the present invention to clipping points, and a force is needed only to insert the belt into the through hole and pull it, so that an excessive burden on the operator can be prevented when maneuvering the instrument.

In the gutclamper of the present invention, by clipping the gut tract by the rod-like bodies, the width of the gut tract can be clipped while being pressed and widened by the side surfaces of the rod-like bodies, so that the constricted portion is reduced, and confirmation as to whether the clipping is sufficient can be made.

Furthermore, different from tightening in a ringed manner with a bundling band, the constricted portion like bundled papers is not formed on the gut tract, and the resection range in the case of intestinal resection can be reliably identified.

Hereinafter, an embodiment of the present invention will be described with reference to the accompanying drawings. The present invention is not limited to the illustrated construction. The widths of the belts and the diameters and lengths of the rod-like bodies are set to optimal values according to the surgery site, and the shape and dimensions, etc., of the gutclamper of the present invention can be variously changed in design.

Figure 1:
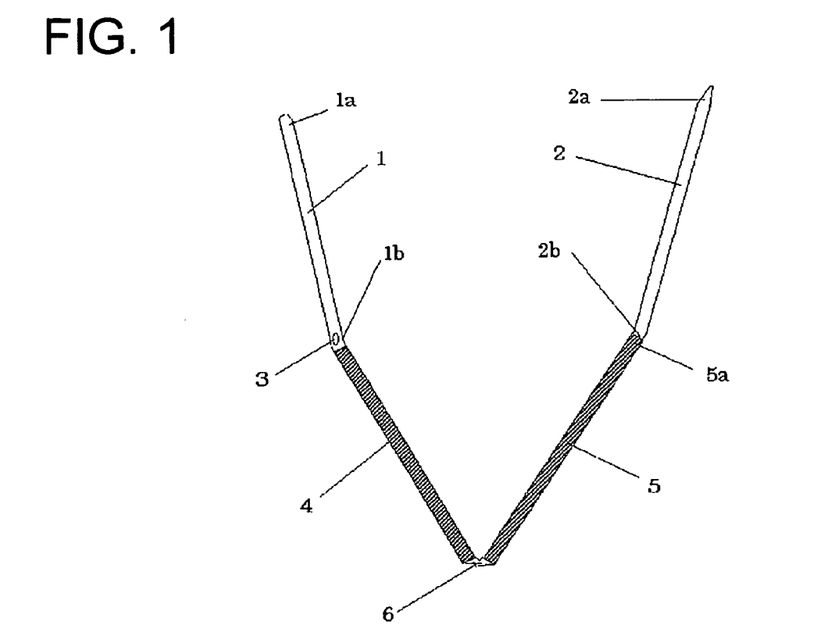
FIG. 1 is an external view of Example 1 of the gutclamper of the present invention.

FIG. 1 is an external view of Example 1 of a gutclamper of the present invention. As shown in FIG. 1, the gutclamper of the present invention has two hard rod-like bodies (4 and 5), and on one ends of the rod-like bodies, belts (1 and 2) with flexibility are provided, and the two rod-like bodies (4 and 5) are joined by a joint (6), and a through hole (3) is made in the belt (1).

The two rod-like bodies (4 and 5) are covered by covers (not shown) made of a resin with flexibility.

Herein, as the two hard rod-like bodies (4 and 5), columnar rods made of stainless steel are used.

Concerning the lengths of the rod-like bodies, the shorter rod-like body has a length of about 55 millimeters, and the longer rod-like body has a length of about 60 millimeters. The diameters of the rod-like bodies are both about 2 millimeters.

The length difference of about 5 millimeters between the rod-like body (4) and the rod-like body (5) is provided for smoothly fitting the tip end (5a) of the longer rod-like body (5) into the through hole as described later.

According to the clipping position on the gut tract, the lengths and diameters of the rod-like bodies are adjustable.

For the belts (1 and 2), a urethane resin that is soft and has bendability and elasticity is used. The belt (1) has the through hole (3), and has as a length of 70 to 90 millimeters.

On the other hand, the belt (2) is to be inserted through the through hole (3), and is made longer than the belt (1) for easy insertion by the operator, and has a length of 80 to 100 millimeters. The tip end (2a) of the belt (2) is tapered so as to be easily inserted through the through hole. Both belts (1 and 2) have a width of about 4 millimeters and a thickness of about 1 millimeter.

The lengths of the belts are adjustable so that handling of the belts becomes easy by considering the procedure for clipping the whole circumference of the gut tract in a laparoscopic operation.

Next, the manner of connecting the belt and the rod-like body and the manner of joining the two rod-like bodies will be described below. In this example, the belts, covers, and joint are integrally molded by means of heat fusion by using a urethane resin that is soft and has bendability and elasticity. Instead of the urethane resin, natural rubber or synthetic rubber or a soft resin such as low-density polyethylene may be used. Other than the heat fusion, injection molding, thermal compression molding or bonding may be used for integral molding.

The belts are colored by mixing a coloring pigment into the resin.

FIG. 2 through FIG. 5 illustrate a use image of Example 1 of the gutclamper of the present invention. Hereinafter, it is described step by step.

Figure 2:
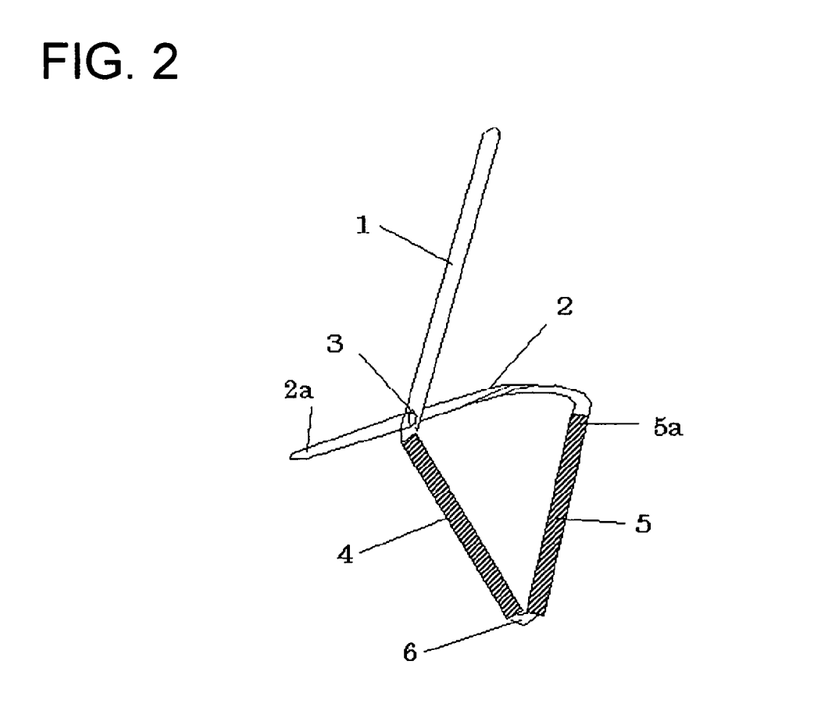
FIG. 2 is a view of a use image of Example 1 of the gutclamper of the present invention (a state that the belt is inserted through the through hole)

First, FIG. 2 shows a state in that the belt (2) is inserted through the through hole (3). Into the through hole (3) made in one belt (1), the other belt (2) is inserted from the tip end side, whereby the two rod-like bodies can clip the gut tract by using the joint (6) as a pivot. In FIG. 2, a circle is formed by the belt (1), the belt (2), the rod-like body (4), and the rod-like body (5), and in this ring, the gut tract to be clipped exists. In other words, the belt (2) is inserted through the through hole (3) so as to surround the gut tract by the belt (1), the belt (2), the rod-like body (4), and the rod-like body (5).

Figure 3:
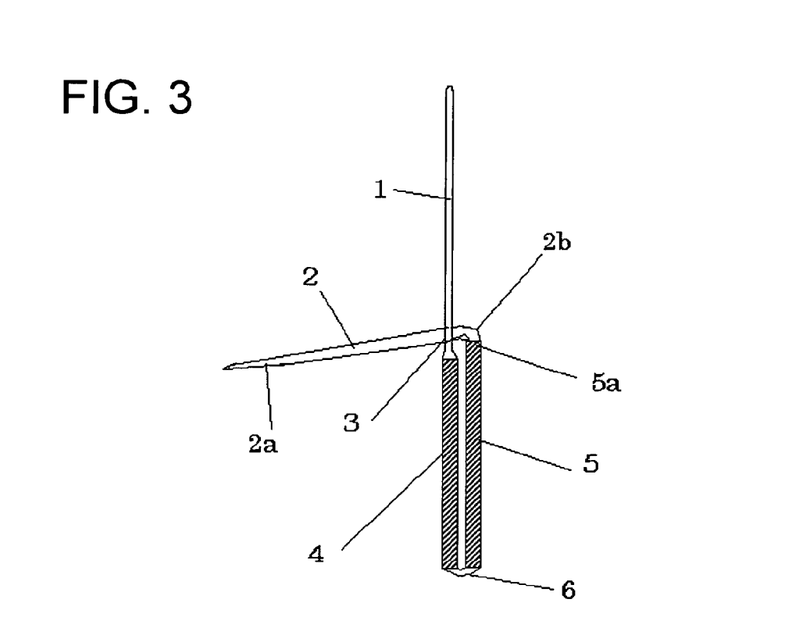
FIG. 3 is a view of a use image of Example 1 of the gutclamper of the present invention (a state that the whole belt is inserted through the through hole)

Next, FIG. 3 shows a state that by seizing the tip end of the belt (1) and pulling the tip end of the belt (2), the whole belt (2) is inserted through the through hole (3), whereby the gut tract (not shown) is clipped by the rod-like body (4) and the rod-like body (5).

Figure 4:
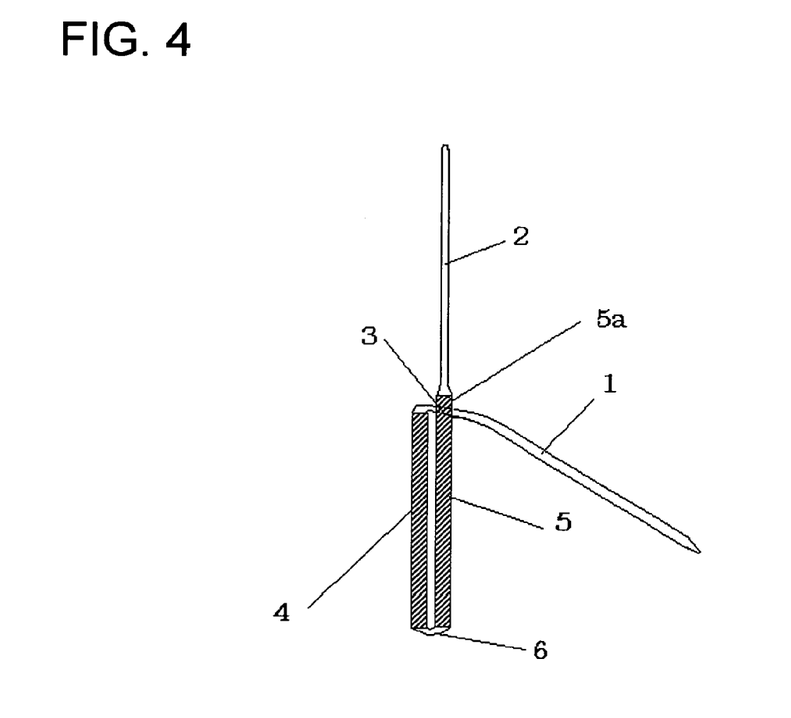
FIG. 4 is a view of a use image of Example 1 of the gutclamper of the present invention (a state that the tip end of the longer rod-like body is fitted in the through hole and locked)

FIG. 4 shows a state that the tip end of the longer rod-like body is fitted in the through hole and locked. The two rod-like bodies are made different in length from each other, a through hole (3) is made in the belt (1) connected to the shorter rod-like body (4), in such a manner that the through hole is positioned at the tip end of the longer rod-like body (5) when the two rod-like bodies are put together by using the joint (6) as a pivot, so that as shown in FIG. 4, by inserting the whole belt (2) through the through hole (3) from the tip end side, the tip end (5a) of the longer rod-like body (5) can be fitted in the through hole and locked.

Next, a method for releasing the clipping state will be described.

Figure 5:
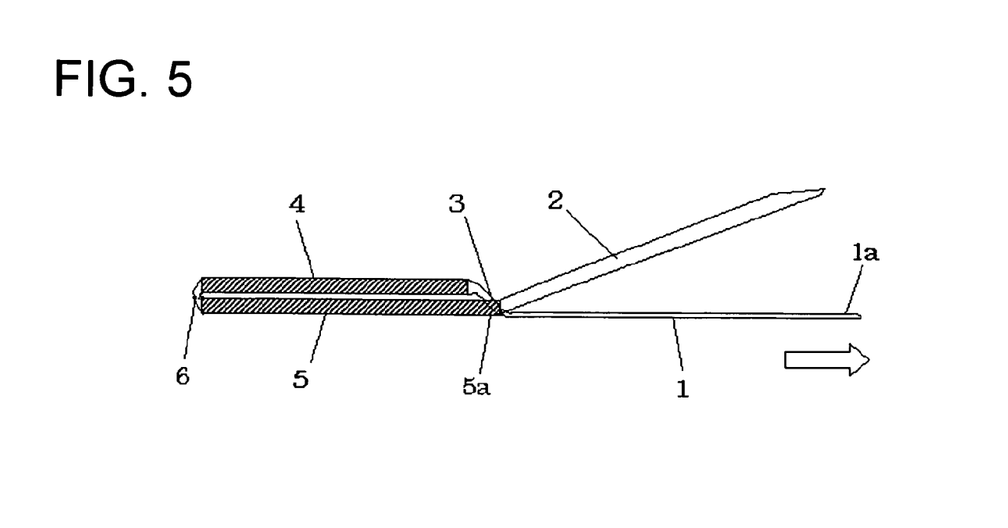
FIG. 5 is a view of a use image of Example 1 of the gutclamper of the present invention (a state that one belt is pulled to make the tip end of the longer rod-like body to come out from the through hole, whereby the clipping is released)

To release the clipping state by displacement or the like of the clipping position of the gut tract, by seizing the joint (6) of the rod-like bodies and pulling the belt (1), the tip end (5a) of the rod-like body (5) comes out from the through hole (3) and the locked state can be released.

FIG. 5 shows a state that the joint (6) of the rod-like bodies is seized, the belt (1) is pulled to make the tip end (5a) of the longer rod-like body come out from the through hole (3), whereby the clipping state is released.

The belt (1) is flexible and elastic, so that the shape of the through hole (3) made in the belt (1) is also deformed into an oval shape in the pulling direction, and the tip end (5a) of the rod-like body is made easier to come out from the through hole (3). Unless the belt (1) is pulled, the tip end (5a) of the rod-like body does not come out from the through hole (3), and the state that the rod-like bodies clip the gut tract is reliably maintained.

EXAMPLE 2

Next, another Example 2 will be described.

Figure 6:
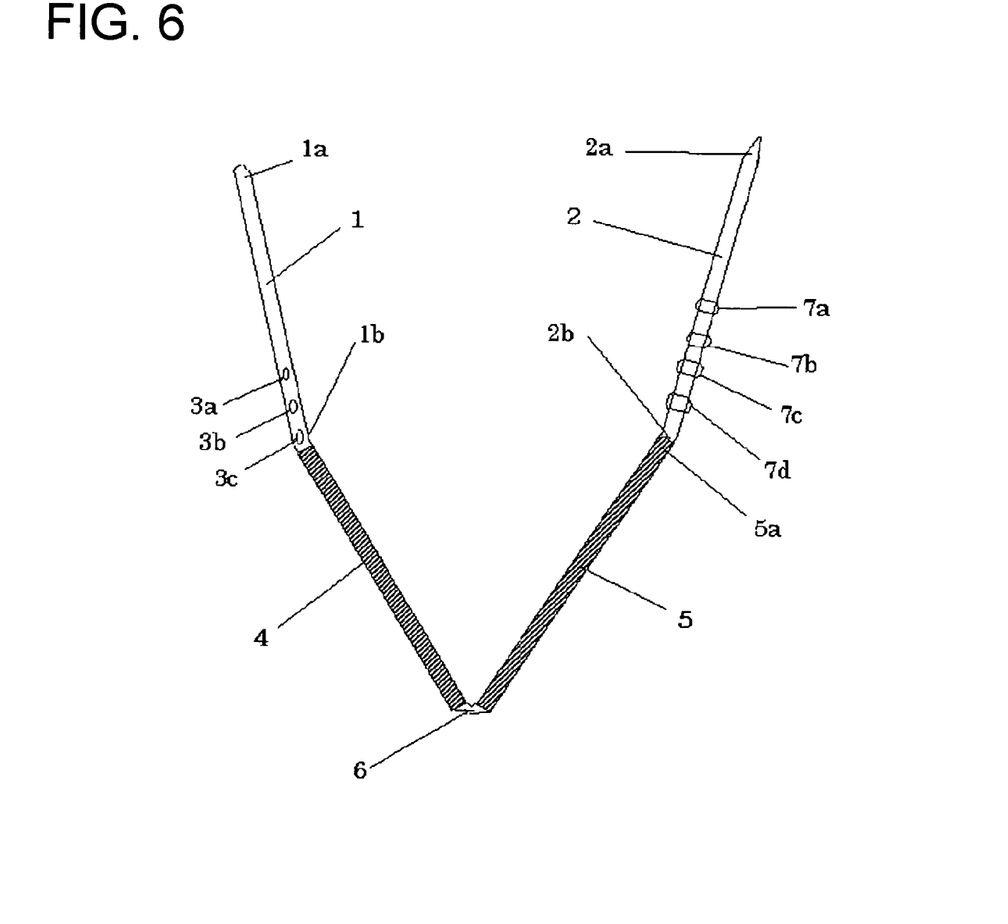
FIG. 6 is an external view of Example 2 of the gutclamper of the present invention.

When the belt is inserted through the through hole, it can be locked due to the respective elastic friction, however, when a further locking force is necessary, as in this Example 2, projections are provided on a part of the belt.

FIG. 6 is an external view of Example 2 of the gutclamper of the present invention, and as shown in FIG. 6, projections (7a through 7d) are provided on a part of the belt (2) to be inserted through the through hole (3) to lock the belt (2) so that the belt (2) becomes more difficult to come out from the through hole (3) after being inserted in the through hole (3). Various shapes such as spherical, semispherical, and rectangular shapes of the projections are possible.

EXAMPLE 3

Figure 7:
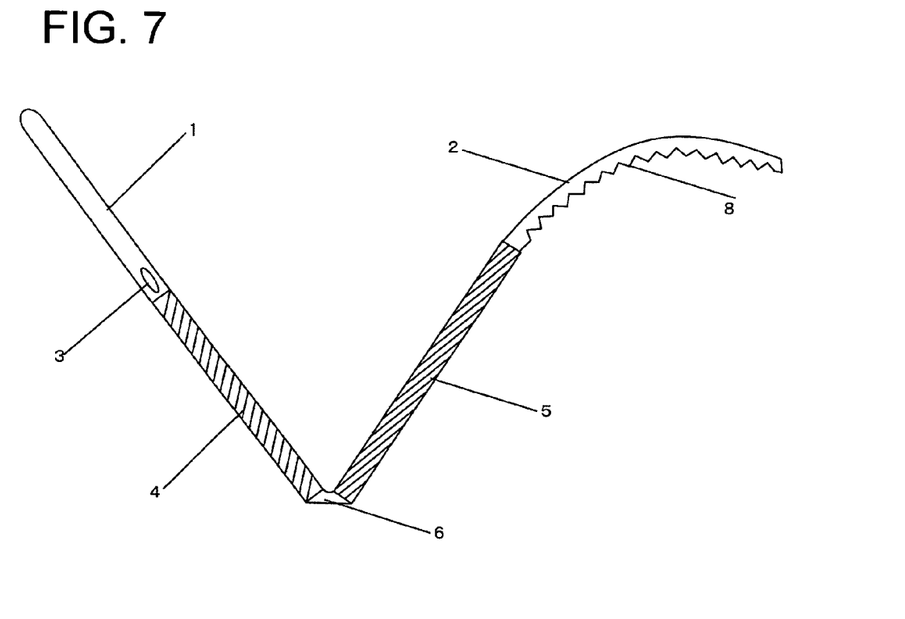
FIG. 7 is an external view of Example 3 of the gutclamper of the present invention.
Figure 8:
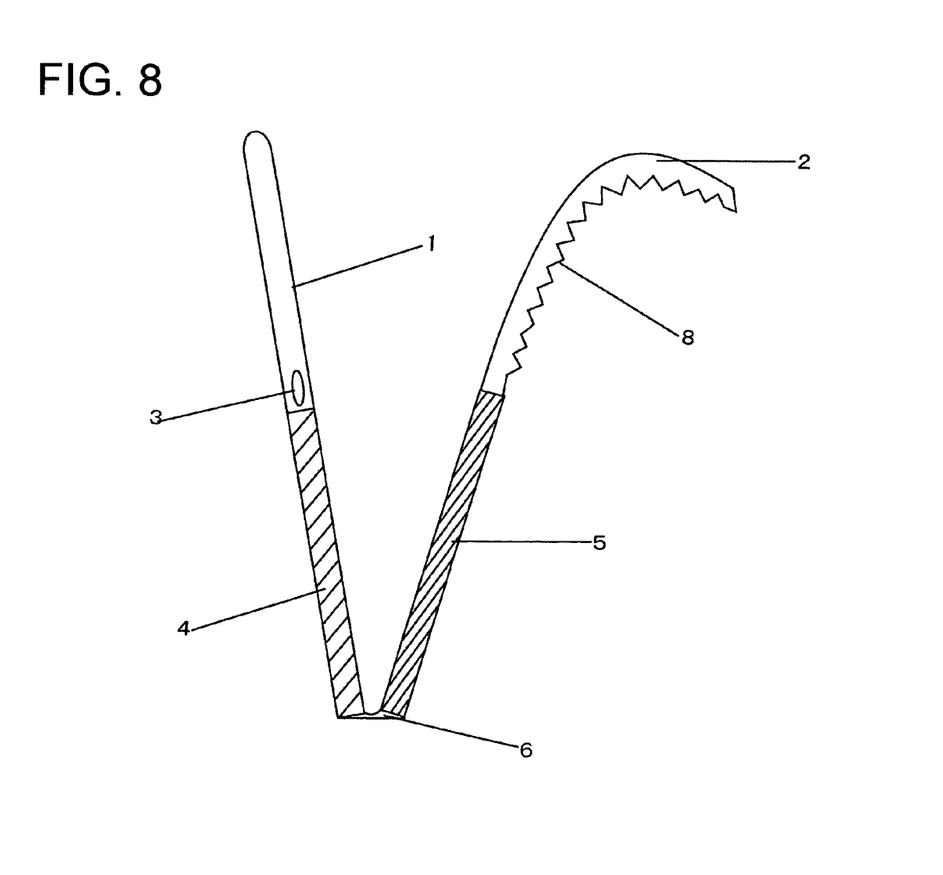
FIG. 8 is an external perspective view of Example 3 of the gutclamper of the present invention.
Figure 9:
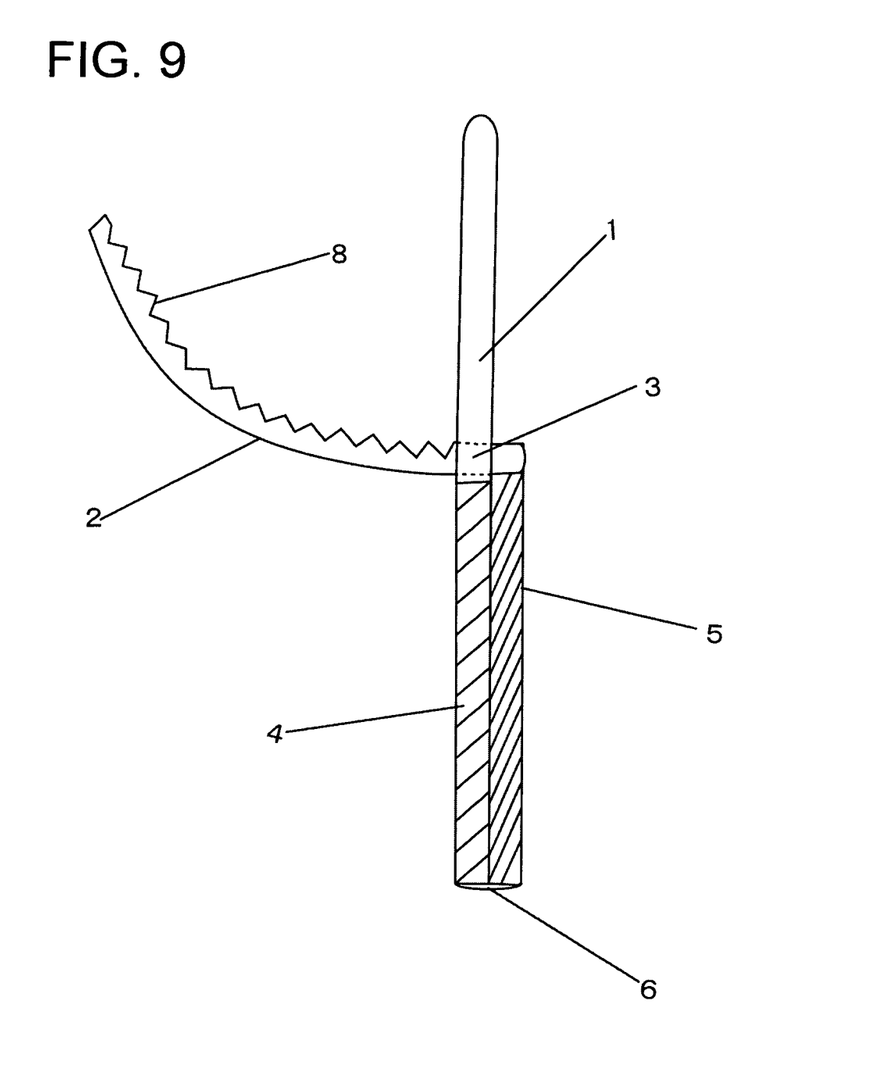
FIG. 9 is a view of a use image of Example 3 of the gutclamper of the present invention (clipping state).

Still another Example 3 will be described. FIG. 7 through FIG. 9 show an external view, an external perspective view, and a use image (clipping state) of Example 3.

In Example 3, as in the case of Example 2 described above, when a further locking force is necessary, a serrated uneven portion (8) is provided on a part of the belt.

In Example 3, it is assumed that the shapes of the hard rod-like bodies (4 and 5) are rectangular columns, and the belts (1 and 2) are thick. By providing a serrated uneven portion (8) on a part of the belt (2) to be inserted into the through hole (3) so as to make the belt more difficult to come out from the through hole (3) after being inserted therein.

The gutclamper of the present invention can easily and reliably clip the gut tract during an operation for intraoperative enema cleaning, resection of the stomach or the large intestine, or removal of bile duct calculus or cancerous tissues in the surgical field, and can be used as a medical aid instrument.

What is claimed is:

1. A gut clamp comprising:
    first and second rigid and elongated straight rods, each having a proximal end and a distal end, wherein the first rod is shorter than the second rod;
    first and second flexible and elongated belts, each having a proximal end and a distal end, wherein the proximal ends of the first and second belts are fixed to the first and second rods, respectively, and the first belt is fixed to the first rod and the second belt is fixed to the second rod, respectively;
    a pivot joint at which the first and second rods are joined, wherein the pivot joint is located at the proximal ends of the first and second rods; and
    at least one through hole made in the first belt, wherein the rods extend longitudinally between the pivot joint and the proximal ends of the belts,
    by inserting the distal end of the second belt into the through hole, the two rods clip an object by using the pivot joint as a pivot,
    a distance from the pivot joint to the through hole is approximately the same as the longitudinal length of the second rod, and
    by inserting a whole of the second belt entirely through the through hole, the distal end of the second rod can be fitted in the through hole and locked to transition the gut clamp from an unclamped position to a clamped position,
    wherein the distal end of the second belt is tapered so that the second belt is easily inserted in the through hole, and
    wherein the gut clamp is released from the clamped position by pulling the first belt and deforming the through hole into an oval shape to release the distal end of the second rod from the through hole.

2. The gut clamp according to claim 1, wherein the surfaces of the rods are covered by covers made of a flexible resin.

3. The gut clamp according to claim 2, wherein the belts, covers, and pivot joint are integrally molded by using the resin.

4. The gut clamp according to claim 1, wherein the material of the rods is a metal.

5. The gut clamp according to claim 1, wherein the material of the rods is a hard resin.

6. The gut clamp according to claim 1, wherein the sectional shape of the rods is circular, oval, or polygonal.

7. The gut clamp according to claim 1, wherein the lengths of the rods are 30 to 70 millimeters.

8. The gut clamp according to claim 1, wherein the length difference between the first and second rods is 3 to 7 millimeters.

9. The gut clamp according to claim 1, wherein at least one projection is provided on a part of the second belt so that the second belt resists escaping from the through hole after the second belt is inserted in the through hole.

10. The gut clamp according to claim 1, wherein a serrated portion is formed on a part of the second belt so that the second belt resists escaping from the through hole after the second belt is inserted in the through hole.

11. The gut clamp according to claim 1, wherein the color of the belts is a complementary color of red.

12. The gut clamp according to claim 11, wherein the colors of the belts are different from each other.

13. The gut clamp according to claim 1, wherein the length of the first belt is shorter than that of the second belt.

* * * * *